Figure 1:
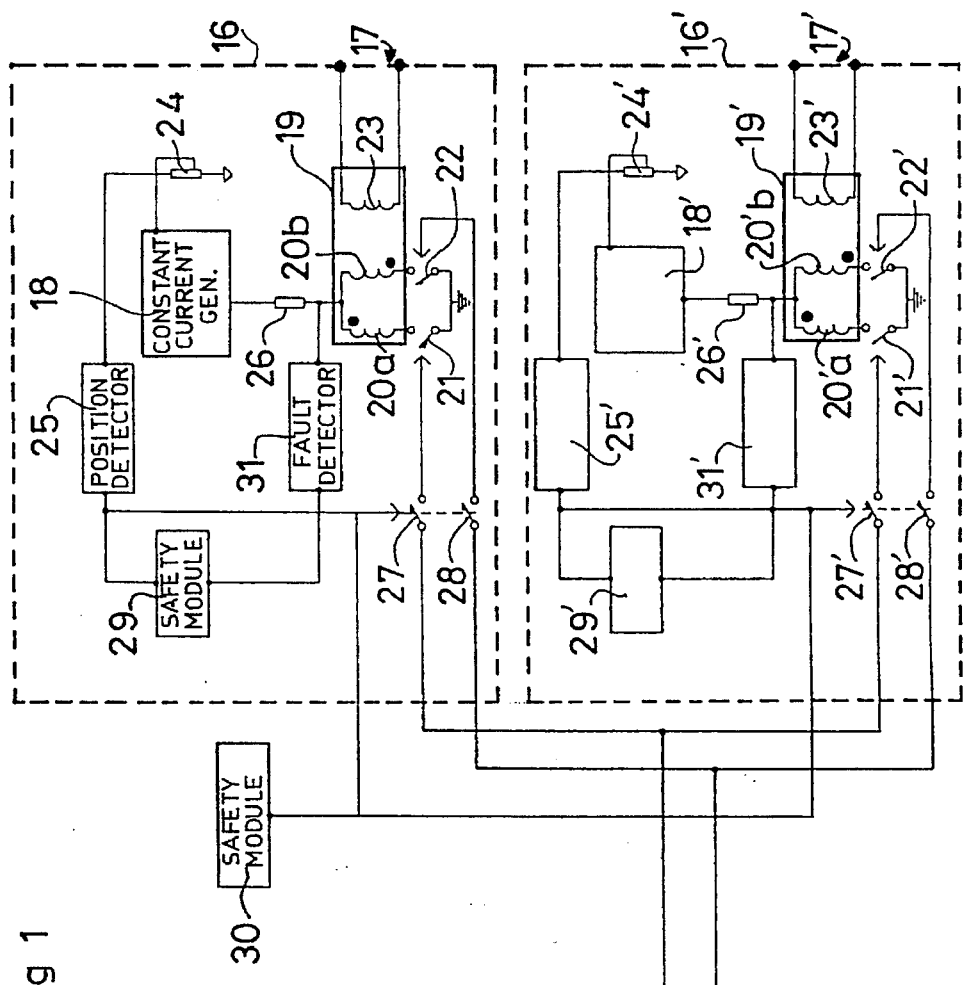
Figure 1:
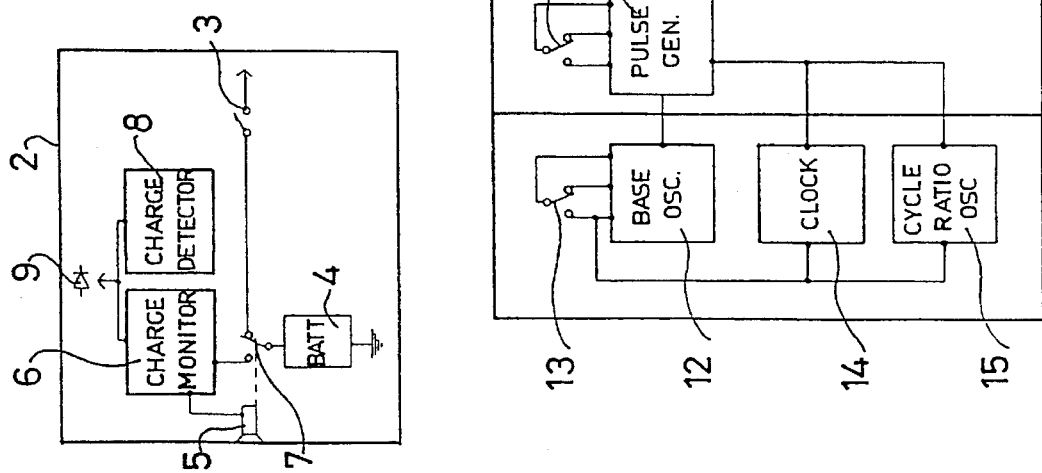

US005504420A

United States Patent [19]
Hamard et al.

[11] Patent Number: 5,504,420
[45] Date of Patent: Apr. 2, 1996

[54] CURRENT-GENERATING APPARATUS FOR THERAPEUTIC TREATMENTS IN THE FIELD OF BIOPHYSICS AND PHYSIOLOGY

[75] Inventors: Claude Hamard, Ayguesvives; Bernard Mario, Montech; Robert Petitjeans, Toulouse, all of France

[73] Assignee: L'Espace Medical - La Maison Du Medecin, Toulouse, France

[21] Appl. No.: 237,884

[22] Filed: May 4, 1994

[30] Foreign Application Priority Data

May 4, 1993 [FR] France ................................. 93 05421

[51] Int. Cl.⁶ ................................................. A61N 1/36
[52] U.S. Cl. ............................................ 323/911; 607/48
[58] Field of Search ............................... 323/271, 282, 323/351, 911; 128/420 A, 421, 423 R, 423 W; 607/2, 21, 46, 48

[56] References Cited

U.S. PATENT DOCUMENTS

| 3,769,986 | 11/1973 | Herrmann | 323/911 |
|---|---|---|---|
| 3,869,661 | 3/1975 | Castaigne | 323/911 |
| 4,327,322 | 4/1982 | Yukl. | |
| 4,620,543 | 11/1986 | Heppenstall. | |
| 4,890,618 | 1/1990 | Weber et al. | 128/420.6 |
| 5,217,009 | 6/1993 | Kronberg | 128/421 |
| 5,300,096 | 4/1994 | Hall et al. | 607/48 |
| 5,350,415 | 9/1994 | Cywinski | 607/48 |

FOREIGN PATENT DOCUMENTS

| 0354578 | 2/1990 | European Pat. Off.. |
| 0459945 | 4/1991 | European Pat. Off.. |
| 3318874 | 11/1984 | Germany. |

Primary Examiner—Matthew V. Nguyen
Attorney, Agent, or Firm—William R. Hinds

[57] ABSTRACT

The invention concerns a current-generating apparatus for supplying at least two probes designed to be applied to a part of the human body for the purpose of therapeutic treatment in the field of biophysics and physiology. This apparatus comprises a self-contained electrical power supply source (2) suitable for delivering a constant voltage, a constant current generator (18), a frequency-generator (10, 19) suitable for transforming the constant current so as to deliver a current in the form of biphase rectangular pulses with zero mean and steep edges, the total duration T of which in µs is substantially between 200 µs and 800 µs, and a delay circuit (12, 14, 15) for delaying the sending of the starts of pulses suitable for triggering a pulse every k ×15 ms, where k=1 or 4.

14 Claims, 3 Drawing Sheets

CURRENT-GENERATING APPARATUS FOR THERAPEUTIC TREATMENTS IN THE FIELD OF BIOPHYSICS AND PHYSIOLOGY

The invention concerns current-generating apparatus having at least one connection output for supplying at least two probes designed to be applied to part of the human body for the purpose of therapeutic treatment in the field of biophysics and physiology.

Current-generating apparatus used at present for the purpose of therapeutic treatment, and notably as described in the patents EP 459.945 and U.S. No. 4.327.322, gives off stimuli at integer frequencies which have little correlation with the biological norm. The drawback of such apparatus lies in the fact that obtaining a correct result entails an enormous waste of energy with a high proportion of energy entering the physiology without being usable or used.

The present invention aims to mitigate this drawback and its main objective is to provide current generating apparatus, the performance of which is appreciably improved compared with that of known apparatus.

For this purpose, the invention relates to apparatus comprising:
- a self-contained electrical power supply source able to deliver a constant voltage,
- means for generating a constant current,
- frequency-generating means suitable for transforming the constant current so as to deliver a current in the form of biphase rectangular pulses with zero mean and steep edges, the total duration T of which in µs is substantially between 200 µs and 800 µs.

According to the invention, this apparatus is characterized in that it comprises means for delaying the sending of starts of pulses, suitable for triggering a pulse every k×15 ms, where k=1 or 4.

The object of the invention was therefore to produce current-generating apparatus having time-delay means designed to control the amount of time elapsing between two starts of pulses, and to trigger a pulse every k×15 ms where k=1 or k=4.

In other words, the idea forming the basis of the invention was to reason in terms of delaying starts of pulses, with very specific values (15 ms or 60 ms) for this time delay, avoiding any reference to notions of frequency (expressed in Hertz) concerning the said impulses.

Such a design leads to the obtaining of apparatus generating stimuli which are in complete correlation with the biological norm and therefore making it possible to obtain optimum results concerning the quantity of energy which is usable and used during therapeutic treatment.

This apparatus offers, in addition, two possibilities for regulating the starts of pulses which may be triggered either every 15 ms or every 60 ms.

By way of example, the periodicity of 60 ms may be used during a treatment aiming to assist the muscular recruitment of a muscle whose capacity for recruitment is impaired. It can therefore be used during a treatment aiming to reinforce the proprioceptive process.

As for the periodicity of 15 ms, this enables the maximum possible production of muscular contractions to be obtained, and may for example be used during a treatment aiming to achieve a strengthening of the muscle.

Since this periodicity of 15 ms leads to the tetanisation of the muscle treated, the apparatus according to the invention is designed so as to interrupt the treatment with rest cycles. For this purpose, the time-delay means comprise advantageously:

- a base oscillator having a switch suitable for enabling the periodicity, 15 ms or 60 ms, of the pulses to be selected,
- a cycle-ratio oscillator arranged so as to be active when the periodicity of the pulses is 15 ms, and adapted so as to divide periodically the emission of the pulses into two cycles of predetermined durations: a working cycle during which the pulses are delivered every 15 ms, and a rest cycle during which no pulses are delivered.

In addition, according to a preferred embodiment, this cycle-ratio oscillator is adapted so that the ratio between the duration of the rest cycle and the duration of the working cycle is three.

In addition, the apparatus according to the invention is also designed to limit automatically the duration of a treatment when the periodicity of the pulses is 15 ms. For this purpose, the time-delay means advantageously comprise a clock suitable for interrupting the emission of pulses at the end of a predetermined lapse of time after the beginning of the treatment, when the periodicity of the pulses is 15 ms.

According to another characteristic of the invention the frequency-generating means are adapted for delivering pulses, the total duration T of which may be either 300 µs or 600 µs, and comprise a selector switch for one or other duration.

Indeed, these two values prove to constitute the optimum therapeutic choice, since the selection of one or other value makes it possible to respond, in addition, to the chronaxia of each muscle.

In addition, according to another characteristic of the invention, the frequency generating means comprise:
- a pulse generator suitable for delivering positive pulses with a total duration of T/2, one being shifted with respect to the other by T/2,
- at least one transformer having two reversed primary windings having a common point connected to a current generator, the said primary windings being activated by the pulse generator in such a way as to generate the biphase rectangular current on the secondary winding of the transformer.

The apparatus according to the invention advantageously includes, in addition, means for manually adjusting the intensity of the current delivered to the connection outputs, adapted so as to cause the said intensity to vary between a zero minimum value and a predetermined value.

This apparatus also has safety modules aimed at monitoring the intensity of the current delivered.

The first of these safety modules consists of means for detecting the position of the means for adjusting the intensity of the current, suitable for preventing the emission of pulses when, at the time the apparatus is started up, the said adjustment means are in a different position from the one corresponding to the zero intensity value.

Such detection means have the advantage of providing, at the time the apparatus is started up, initialisation by a zero intensity value.

A second safety module comprises so-called program change detection means, suitable for interrupting the emission of pulses during the operation of the base oscillator switch or of the frequency-generating means, while the adjustment means are in a different position from the one corresponding to the zero intensity value.

Finally, means for detecting faults, such as excess voltage, a disconnected probe, etc, are suitable for preventing the emission of pulses when such a fault occurs.

Other characteristics, aims and advantages of the invention will emerge from the following detailed description, given with reference to the accompanying drawings which show a preferred embodiment thereof by way of non-limiting example.

Figure 2:
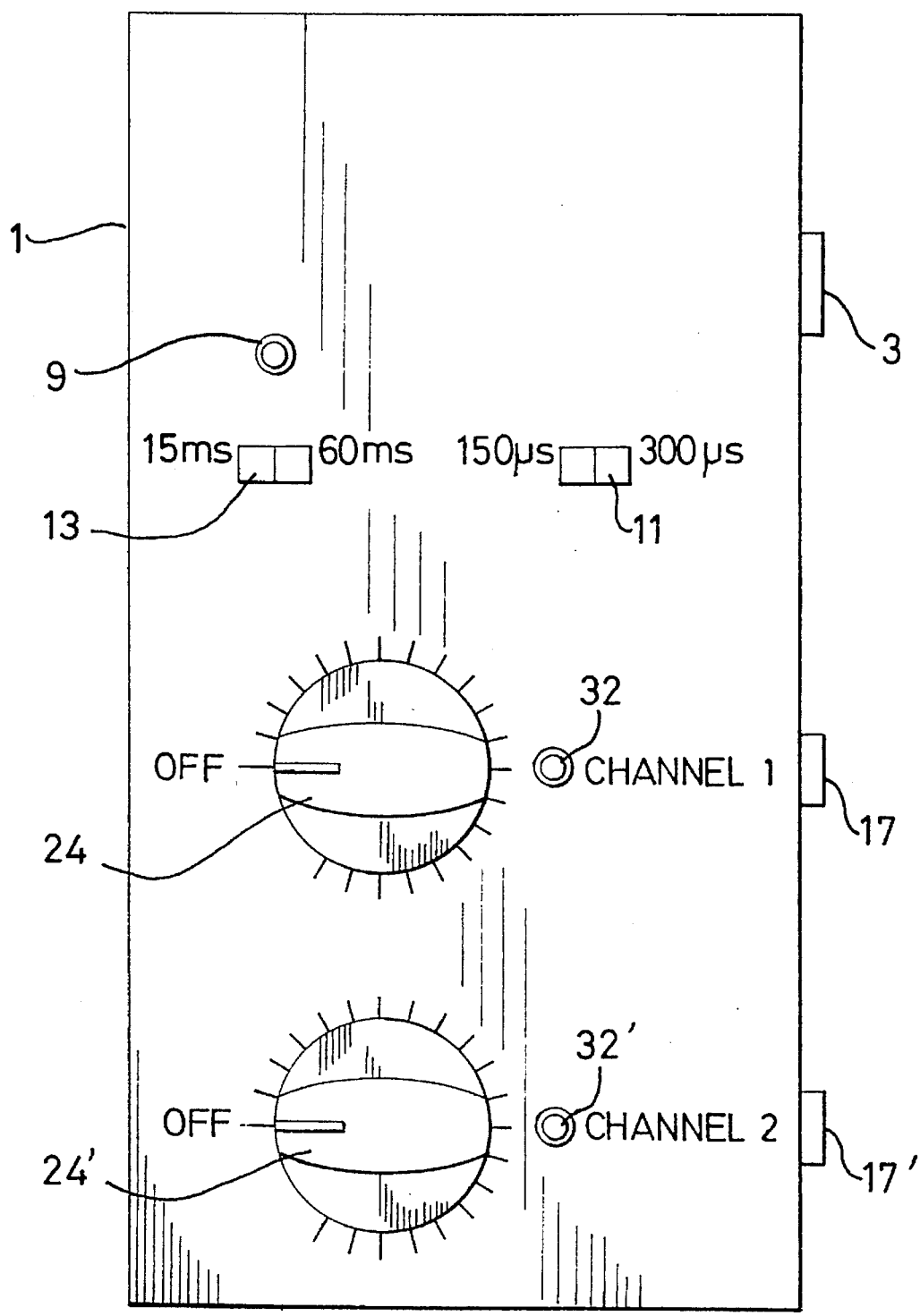

In the drawings which form an integral part of the present description:

FIG. 1 is a block diagram of current generator apparatus in accordance with the invention, FIG. 2 is a view of the front face of the casing of this apparatus, and FIGS. 3a to 3d show the different signal shapes generated by this apparatus.

The current-generating device according to the invention constitutes medical equipment for physiotherapy (muscular stimulator). This apparatus is presented in the form of a portable casing 1 having sufficiently small dimensions (around 100 mm×200 mm×50 mm) to be able to be held in one hand, with the possibility of being carried on a belt when in operation.

As shown in FIG. 1, this apparatus comprises, firstly, a self-contained electrical power supply source 2, having a main on/off switch 3, and including a battery 4 delivering a constant voltage of 7.2 volts.

This power supply source 2 includes in addition an external socket 5 for connecting the battery 4 to a charger, and a charge monitor 6 suitable for controlling an electronic switch 7 enabling the battery 4 to be connected either to the supply system of the apparatus or to the external socket 5.

This power supply source 2 includes, finally, means 8 for detecting the charge of the battery 4, and an indicator light 9 disposed on the front face of the casing 1. This indicator light 9 is connected to the charge monitor 6 and to the detection means 8 in such a way that:

when a charger is connected to the apparatus, the said indicator light is lit when the apparatus is on charge, and is extinguished when the charging is completed, when the apparatus is in use, the said indicator light is extinguished when the charge of the battery 4 is correct and flashes on and off when this battery needs to be recharged.

The apparatus comprises, secondly, a pulses generator 10 having two outputs, at each of which it delivers a positive rectangular pulse with a total duration of T/2, the said pulses being offset by T/2.

This pulse generator 10 is, in addition, adapted so that the duration T is 300 μs or 600 μs, and it comprises a switch 11 disposed on the front face of the casing 1 for the manual selection of one or other duration.

The apparatus includes, in addition, time-delay means connected to the pulse generator 10.

These time-delay means include firstly a base oscillator 12, suitable for commanding the pulse generator 10 to trigger two pulses offset by T/2, either every 15 ms or every 60 ms. In order to enable the periodicity, 15 or 60 ms, to be selected manually, this base oscillator 12 has a switch 13 disposed on the front face of the casing 1.

The time-delay means comprise, in addition, a clock 14 adapted for demanding stoppage of the emission of pulses after 8 min of treatment, when the periodicity of these pulses is 15 ms.

These time-delay means comprise, finally, a cycle-ratio oscillator 15, acted on when the duration of the pulses is 15 ms and is adapted so as to divide, periodically, the emission of the pulses into two cycles: a working cycle, the duration of which is 3 secs and during which the pulses are normally delivered every 15 ms, and a rest cycle, the duration of which is 9 secs and during which the emission of the pulses is stopped.

The apparatus comprises, in addition, two strictly identical circuits 16, 16' to which the pulses are delivered in parallel. These circuits each have an output channel 17, 17' on which are generated signals which are identical and in phase, allowing simultaneous and synchronous treatment of two muscles with identical chronaxia in the same patient.

Each of these circuits 16, 16' includes, firstly, a constant-current generator 18, 18' supplied by the battery 4.

These circuits 16, 16' include, in addition, a transformer 19, 19', which has two reversed primary windings 20a, 20b, 20'a, 20'b, having a common point connected to the current generator 18, 18'. These transformers 19, 19' are connected to electronic control switches 21, 22, 21', 22' connecting the free end of the primary windings 20a, 20b, 20'a, 20'b to the earth of the apparatus and arranged so as each to be actuated by one of the pulses delivered by the pulse generator 10.

The arrangement of these transformers 19, 19' makes it possible to generate on the secondary winding 23, 23', and consequently to generate towards the channels 17, 17', a current in the form of biphase rectangular pulses with zero mean and steep edges, the total duration T of which is either 300 μs or 600 μs.

Each circuit 16, 16' includes, in addition, a potentiometer 24, 24', disposed on the front face of the casing 1, adapted so as to make it possible to obtain an output current adjustable from 0 to 100 mA on each channel 17, 17'. Each of these potentiometers, 24, 24' is in addition associated with a module 25, 25' for detecting its position.

The circuits 16, 16' have, in addition, a resistor 26, 26' for calibration of the current, interposed between the current generator 18, 18' and the transformer 19, 19'.

These circuits also comprise safety modules suitable for interrupting, by acting on the electronic switches 27, 28, 27', 28', the emission of pulses towards the transformer 19, 19'.

The first of these modules 29, 29' is adapted for detecting the position of the potentiometers 24, 24' when the apparatus is being started up, and for demanding the opening of the switches 27, 28, 27', 28' when these potentiometers 24, 24' are in a position other than the "off" position, idea position different from the one corresponding to a current of zero intensity.

The second of these modules 30 is common to the two circuits 16, 16' and is adapted for detecting any change in the program during treatment, ie any action on the switches 11, 13 of the pulse generator 10 and of the base oscillator 12, and for demanding the opening of the switches 27, 28, 27', 28' when this change in program occurs at a time when the potentiometers 24, 24' are not in their "off" position.

The third module 31, 31' is adapted for detecting faults, such as excess voltage or a disconnected probe, and for demanding the opening of the switches 27, 28, 27', 28' when such a fault occurs.

Each circuit 16, 16' includes, finally, a indicator light 32, 32' disposed on the front face of the casing 1 and adapted for indicating the state of the corresponding output 17, 17' in the following way:

light on: channel in operation, light extinguished: channel switched off (potentiometer 24, 24' in the "off" position), indicator light flashing on and off: fault at output (excess voltage or probe disconnected).

The apparatus described above enables four types of identical and in-phase signals to be generated on the two channels 17, 17', which are shown in FIGS. 3a to 3d.

Figure 3A:
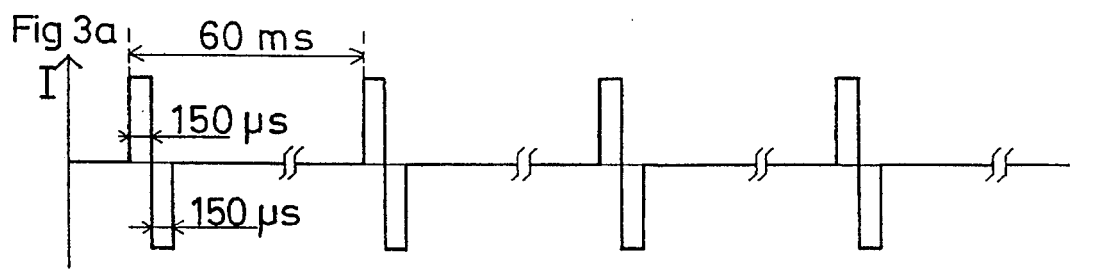
Figure 3B:
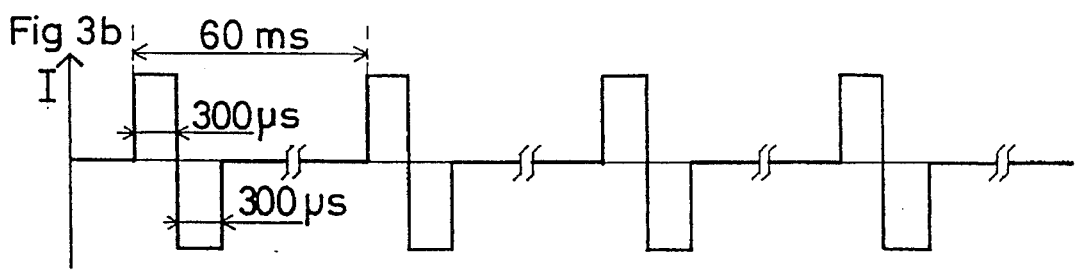

The first two types of signal shown in FIGS. 3a and 3b are in the form of pulses with a total duration of 300 μs (FIG. 3a) or 600 μs (FIG. 3b), and a periodicity of 60 ms. Unless the treatment is stopped by the user, these pulses are delivered without interruption from the time when the machine is started.

Figure 3C:
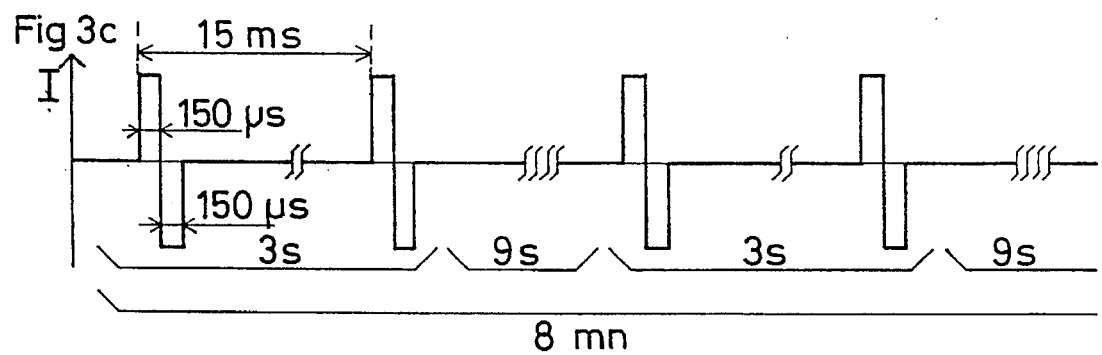
Figure 3D:
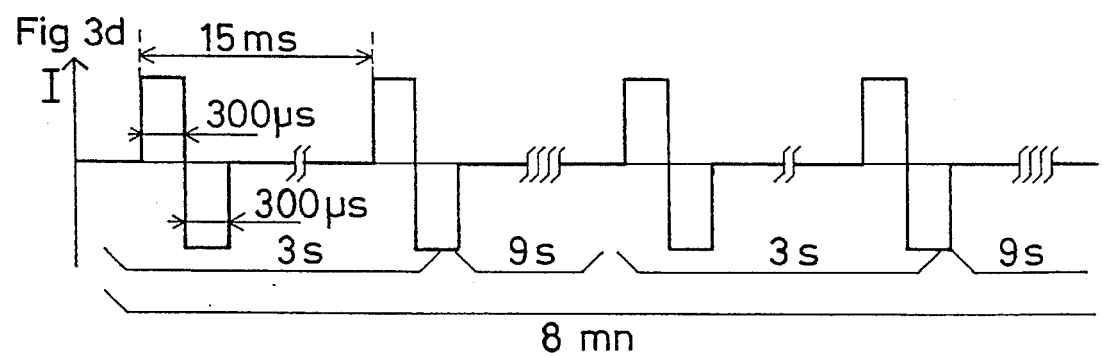

The two other types of signal shown in FIGS. 3c and 3d are presented in the form of pulses with a total duration of 300 µs (FIG. 3c) or 600 µs (FIG. 3d), and a periodicity of 15 ms. In addition, the total duration of treatment is limited to 8 min, and this treatment includes, in alternation, working cycles of a duration of 3 secs and rest cycles of a duration of 9 secs.

We claim:

1. Current-generating apparatus having at least one connection output (17) for supplying at least two probes designed to be applied to a part of the human body for the purpose of therapeutic treatment in the field of biophysics and physiology, and including:

a self-contained electrical power supply source (2) able to deliver a constant voltage, means (18) for generating a constant current, frequency-generating means (10, 19) suitable for transforming the constant current so as to deliver a current in the form of biphase rectangular pulses with zero mean and steep edges, the total duration T of which in µs is substantially between 200 µs and 800 µs, said apparatus comprising means (12, 14, 15) for delaying the sending of starts of pulses suitable for triggering a pulse every k×15 ms, where k=1 or 4.

2. Current-generating apparatus as claimed in claim 1, wherein the frequency-generating means (10, 19) are adapted for delivering impulses, the total duration T of which may be either 300 µs or 600 µs, and comprising a switch (11) for selecting one or other duration.

3. Current-generating apparatus as claimed in claim 1, wherein the time-delay means comprise:

a base oscillator (12) having a switch (13) suitable for enabling the periodicity, 15 ms or 60 ms, of the pulses to be selected, a cycle-ratio oscillator (15) arranged so as to be active when the periodicity of the pulses is 15 ms, and adapted so as to divide periodically the emission of the pulses into cycles of predetermined durations: a working cycle during which the pulses are delivered every 15 ms and a rest cycle during which no pulses are delivered.

4. Current-generating apparatus as claimed in claim 3, wherein the cycle-ratio oscillator (15) is adapted so that the ratio between the duration of the rest cycle and the duration of the working cycle is three.

5. Current-generating apparatus as claimed in claim 4, wherein the cycle-ratio oscillator (15) is adapted so that the duration of the rest cycle is 9 secs and that of the working cycle is 3 secs.

6. Current-generating apparatus as claimed in claim 3, wherein the time-delay means comprise a clock (14) suitable for interrupting the emission of the pulses at the end of a predetermined lapse of time after the start of treatment, when the periodicity of the said pulses is 15 ms.

7. Current-generating apparatus as claimed in claim 6, wherein the clock (14) is programmed so as to interrupt the emission of the pulses after 8 min of treatment.

8. Current-generating apparatus as claimed in claim 1, wherein the frequency-generating means comprise:

a pulse generator (10) suitable for delivering positive pulses of a total duration of T/2, offset with respect to each other by T/2, at least one transformer (19) with two reversed primary windings (20a, 20b) having a common point connected to a current generator (18), said primary windings being activated by the pulse generator (10) so as to generate the biphase rectangular current on the secondary winding (23) of the transformer (19).

9. Current-generating apparatus as claimed in claim 1, comprising means (24) for manually adjusting the intensity of the current delivered to each connection output (17), adapted for making it possible to vary said intensity between a zero minimum value and a predetermined value.

10. Current-generating apparatus as claimed in claim 9, comprising means (29) for detecting the position of the means (24) for adjusting the intensity of the current, suitable for preventing the emission of pulses when, during the startup of the apparatus, the said adjustment means are in a different position from the one corresponding to the zero intensity value.

11. Current-generating apparatus as claimed in claim 2, wherein the time-delay means comprise: a base oscillator (12) having a switch (13) suitable for enabling the periodicity, 15 ms or 60 ms, of the pulses to be selected, a cycle-ratio oscillator (15) arranged so as to be active when the periodicity of the pulses is 15 ms, and adapted so as to divide periodically the emission of the pulses into cycles of predetermined durations: a working cycle during which the pulses are delivered every 15 ms and a rest cycle during which no pulses are delivered, and further comprising means (24) for manually adjusting the intensity of the current delivered to each connection output (17), adapted for making it possible to vary the said intensity between a zero minimum value and a predetermined value.

12. Current-generating apparatus as claimed in claim 1, comprising means (31) for detecting faults, such as excess voltage or a disconnected probe, suitable for preventing the emission of pulses when such a fault appears.

13. Current-generating apparatus as claimed in claim 1, wherein the electrical power supply source (2) consists of a 7.2 V battery (4) associated with charge monitoring means (6), end-of-charging alarm means (9), and an external socket (5) for connecting to a charger.

14. Current-generating apparatus as claimed in claim 11, comprising so-called program change detection means (30), suitable for interrupting the emission of pulses during the operation of the switch (11, 13) of the base oscillator (12) or of the frequency-generating means (10), when the adjustment means (24) are in a position different from the one corresponding to the zero intensity value.

* * * * *